(12) United States Patent
Frisbie

(10) Patent No.: US 7,857,776 B2
(45) Date of Patent: Dec. 28, 2010

(54) DYNAMICALLY ADJUSTABLE JOINT EXTENSION AND FLEXION DEVICE

(76) Inventor: Robert M. Frisbie, 9990 Devonshire St., Douglasville, GA (US) 30135

( * ) Notice: Subject to any disclaimer, the term of this patent is extended or adjusted under 35 U.S.C. 154(b) by 953 days.

(21) Appl. No.: 11/623,635

(22) Filed: Jan. 16, 2007

(65) Prior Publication Data

US 2007/0167893 A1 Jul. 19, 2007

Related U.S. Application Data

(60) Provisional application No. 60/758,976, filed on Jan. 13, 2006.

(51) Int. Cl.
- A61F 5/00 (2006.01)
- A61F 5/37 (2006.01)
- A63B 23/10 (2006.01)
- A63B 21/00 (2006.01)
- A63B 21/22 (2006.01)
- A63B 21/02 (2006.01)

(52) U.S. Cl. ............... 602/12; 602/5; 602/20; 602/21; 602/23; 602/28; 128/846; 128/878; 128/882; 482/79; 482/92; 482/110; 482/121; 482/124

(58) Field of Classification Search ........ 602/5, 602/12, 26–29, 60–62; 128/869, 878, 881, 128/882; 482/79–80, 92, 110, 121, 122, 482/124, 125, 129

See application file for complete search history.

(56) References Cited

U.S. PATENT DOCUMENTS

| | | | | |
|---|---|---|---|---|
| 2,584,010 A * | 1/1952 | Goffredo | ........ | 602/28 |
| 3,527,209 A * | 9/1970 | Baker | ........ | 602/28 |
| 4,371,161 A * | 2/1983 | Williams | ........ | 482/79 |
| 4,566,447 A * | 1/1986 | Deis | ........ | 602/28 |
| 5,277,699 A * | 1/1994 | Williamson | ........ | 602/28 |
| 5,291,904 A * | 3/1994 | Walker | ........ | 128/882 |
| 5,382,224 A * | 1/1995 | Spangler | ........ | 602/23 |
| 5,662,595 A * | 9/1997 | Chesher et al. | ........ | 602/20 |
| 5,718,673 A * | 2/1998 | Shipstead | ........ | 602/27 |
| 5,771,609 A * | 6/1998 | Messmer | ........ | 36/89 |
| 5,860,423 A * | 1/1999 | Thompson | ........ | 128/882 |
| 5,937,546 A * | 8/1999 | Messmer | ........ | 36/89 |
| 6,004,282 A * | 12/1999 | Whitley | ........ | 602/5 |
| 6,110,078 A * | 8/2000 | Dyer | ........ | 482/79 |
| 6,602,217 B2 * | 8/2003 | Crawford et al. | ........ | 602/28 |
| 6,790,165 B2 * | 9/2004 | Huang | ........ | 482/79 |

(Continued)

Primary Examiner—Patricia M Bianco
Assistant Examiner—Brandon Jackson
(74) Attorney, Agent, or Firm—Weatherly Kerven & Seigel LLC; Mitchell G. Weatherly

(57) ABSTRACT

An adjustable orthosis for, among other functions, flexing or extending a users joint, positioning a limb or digit during or after a surgical procedure, correcting foot drop due to soft tissue contraction, and augmenting soft tissue during weight bearing therapies. In a preferred form, the orthosis includes a padded shell adapted to be worn on a user's limb and a distal support to be worn on one or more digits of the hand or foot or on the forefoot or body of the hand. The padded shell is connected to the distal support solely via an elastic member such as surgical tubing, which also applies a tension force between the two supports. One end of the elastic member carries teeth that mate with a ratcheting device that permits the wearer (1) to gradually increase the tension between the supports and (2) to quickly release the tension.

16 Claims, 12 Drawing Sheets

U.S. PATENT DOCUMENTS

| | | | |
|---|---|---|---|
| D514,225 S * | 1/2006 | Sassi | D24/192 |
| 7,093,694 B2 * | 8/2006 | Brandt et al. | 188/1.11 R |
| 7,354,413 B2 * | 4/2008 | Fisher | 602/29 |
| 7,458,950 B1 * | 12/2008 | Ivany | 602/28 |
| 7,491,186 B2 * | 2/2009 | Zeide et al. | 602/20 |
| 7,611,477 B2 * | 11/2009 | Dayhoff et al. | 602/29 |
| 2002/0129821 A1 * | 9/2002 | Trieloff | 128/882 |
| 2008/0077066 A1 * | 3/2008 | Lewis | 602/28 |
| 2008/0154166 A1 * | 6/2008 | Beckwith et al. | 602/27 |
| 2008/0154167 A1 * | 6/2008 | Fisher | 602/28 |

* cited by examiner

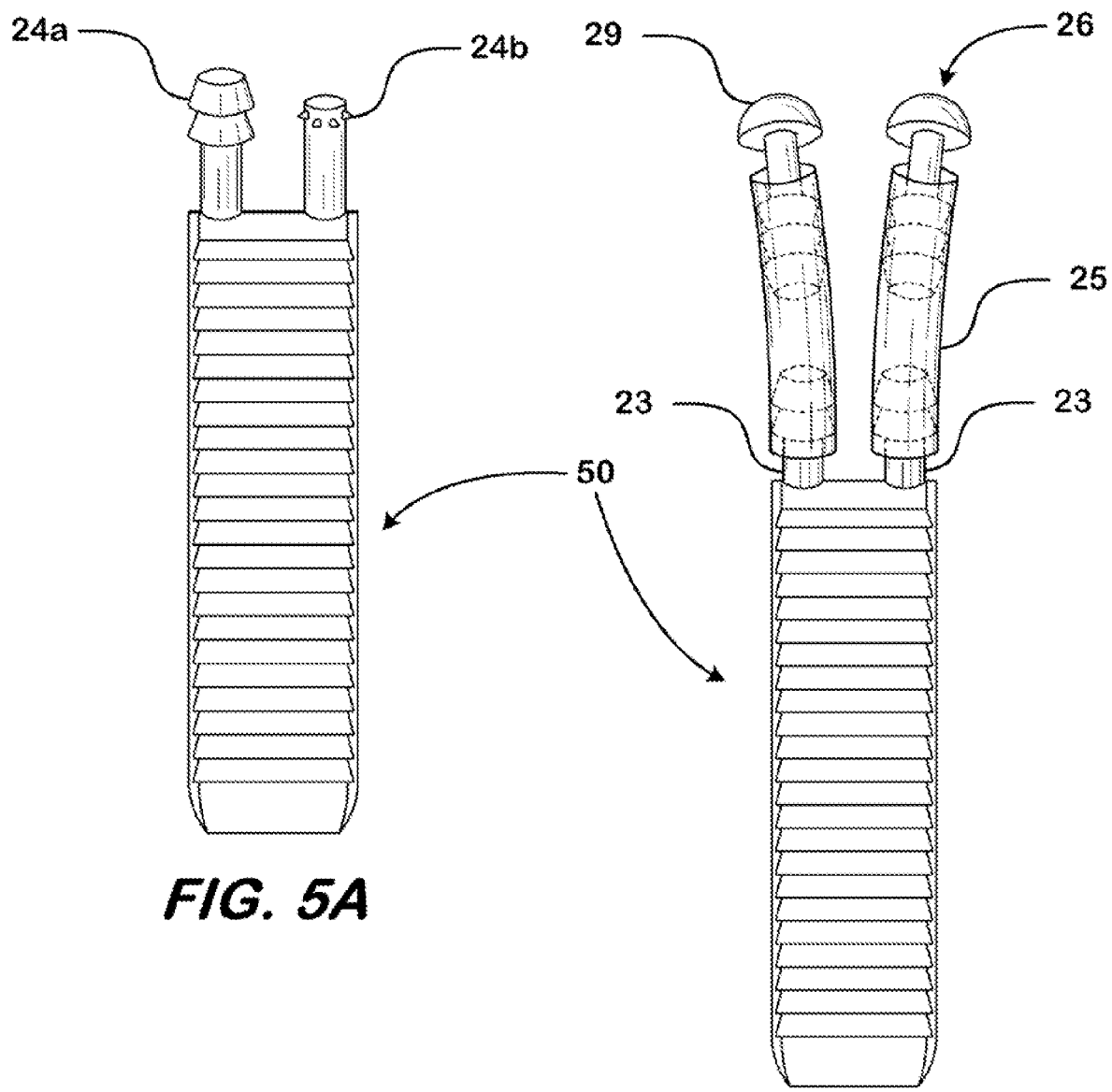
FIG. 5A
FIG. 5B
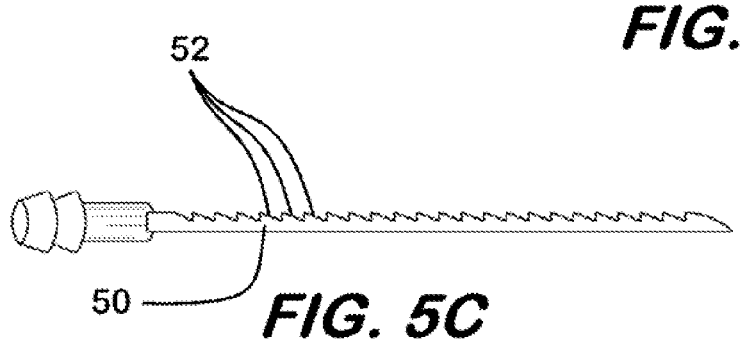
FIG. 5C

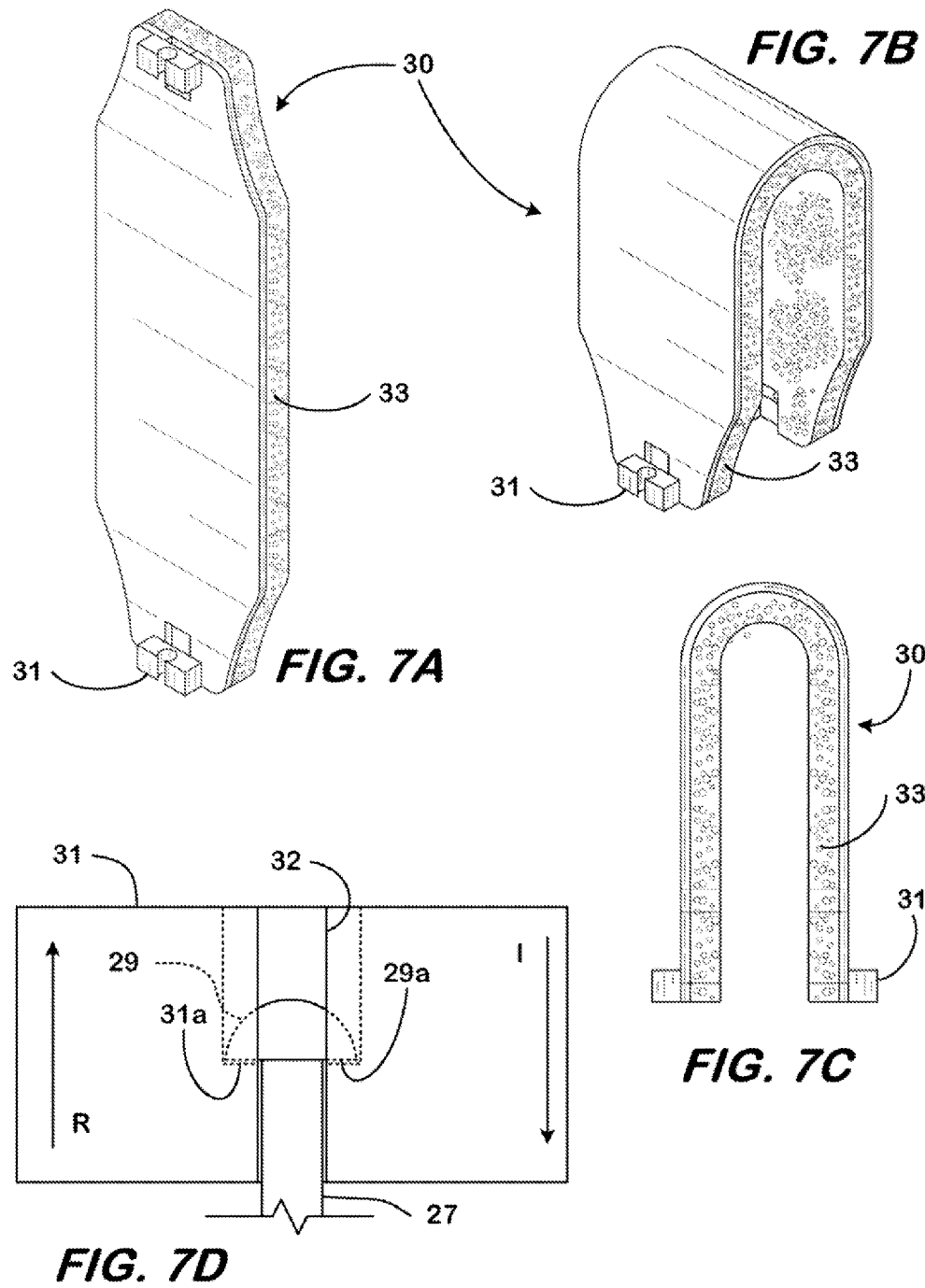

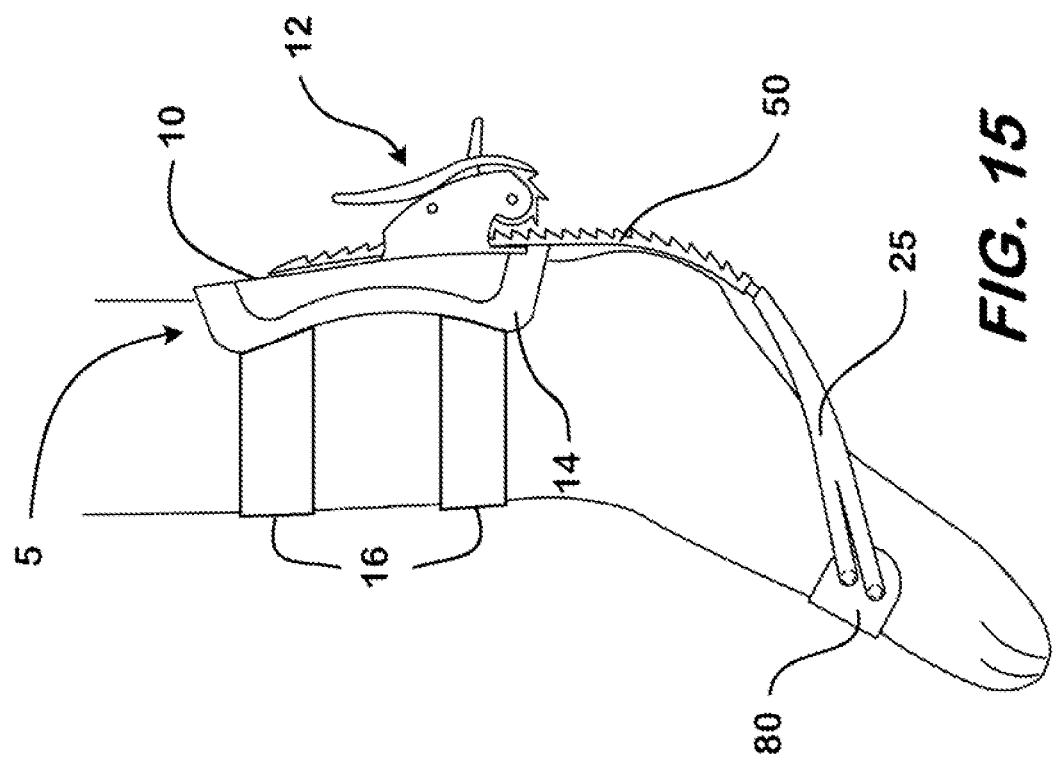
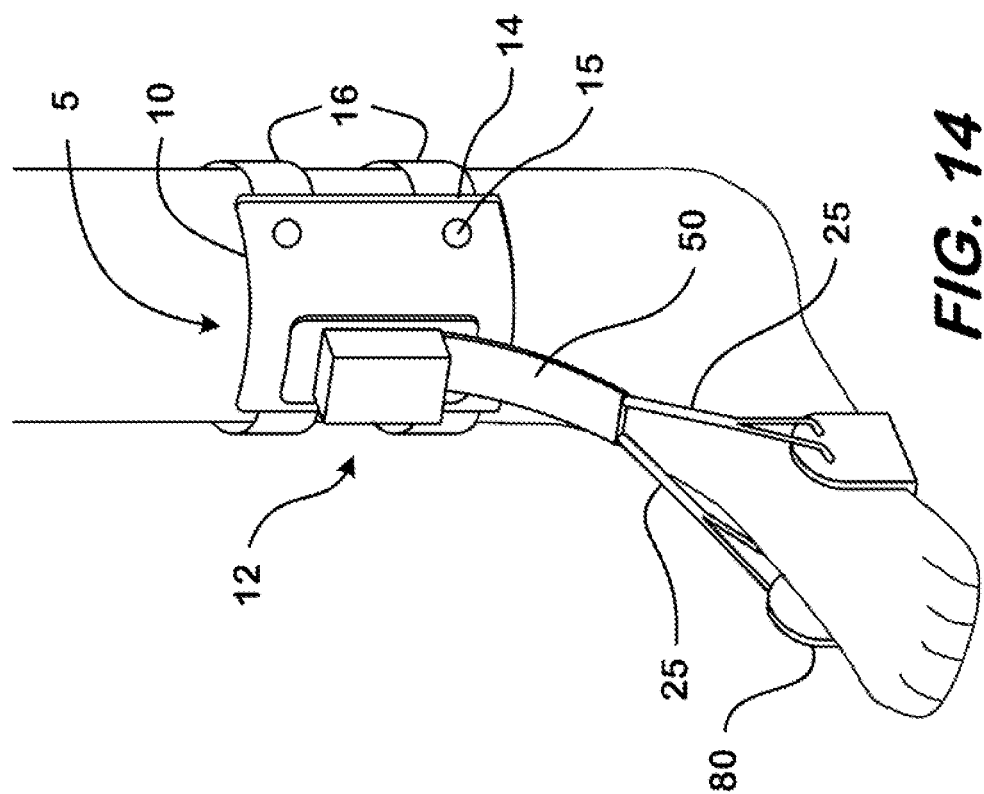

DYNAMICALLY ADJUSTABLE JOINT EXTENSION AND FLEXION DEVICE

I. CROSS REFERENCE TO RELATED APPLICATIONS

Pursuant to 35 U.S.C. §119(e), this application claims priority to U.S. Provisional Application No. 60/758,976 filed Jan. 13, 2006, which is incorporated in its entirety by this reference.

II. FIELD OF THE INVENTION AND BACKGROUND

The present invention generally relates to orthopedic traction devices. More specifically, it relates to a new orthosis which is used by an individual to apply a dynamically adjustable force in both flexion and extension to the joints of said individual's body for the purpose of stretching the soft tissues associated with these joints in order to restore lost or limited range of motion. The new orthosis provides an improved fit and function when compared with conventional orthoses.

Neurological impairment, physical trauma, surgery and prolonged immobility frequently lead to a loss of range of motion in a joint complex due to the contraction of associated "soft tissue." As referred to herein, soft tissue includes: human ligaments, tendons, joint capsules, and other related structures. These soft tissues form a mesh-work of attached fibers which are connected at intervals throughout the tissue, and the longer the distance between the points of attachment, the greater the range of motion. The attachments can release or shift in response to prolonged tension, or additional attachments can develop at points of prolonged contact. The length of the fibers between the attachments can also increase or decrease depending on the presence or absence of force. When a joint is immobilized for a period of time, such as when a patient's limb is immobilized in a cast or splint in order to allow a broken bone to heal, connected tissue at the joint tends to shorten, resulting in a decreased range of motion at the joint. This condition is exacerbated by the length of time the joint is immobilized. Moreover, when surgery involves the cutting open of a joint capsule, the scar tissue that forms when this tissue heals is inherently less supple and less conducive to motion. If not treated appropriately, this post-surgical scar formation can severely limit a patient's normal range of motion.

According to Davis's Law, soft tissue remodels itself based upon the forces applied to it. Therefore, although scarring is inevitable, the nature and structure of the scar tissue itself is malleable. In fact, collagen, which comprises scar tissue, can be lengthened when the appropriate forces are imparted upon it. Rehabilitation efforts to reduce or stretch such contractions usually involve extensive physical therapy or surgical intervention. Both physical therapy and surgical alternatives frequently include the use of some form of orthopedic device such as a splint. Although some splints may have attributes of both, orthopedic splints generally fall into one of two general categories known as static or dynamic. Static splints are primarily designed to hold the affected limb or digits at a preset position and may be manually adjusted to accommodate different desired settings. Serial casting is a form of static splinting where a series of castings hold the limb or digits in a succession of positions. Static splints are commonly used to: restore range of motion, prevent the occurrence of soft tissue contraction associated with long term immobilization, hold limbs in the desired post-surgical position during healing, and aid as a mechanical support for ambulation. Dynamic splints have a similar purpose to static splints but use components such as springs or elastic bands in order to provide an active tension as the soft tissues stretch, in essence taking up the slack. As with static splints, dynamic splints are designed to improve range of motion by exploiting the viscoelastic properties of soft tissue. The dynamic splints are worn over a period of time, such as when a patient is sleeping, in order to stretch the connected tissue by providing a prolonged, constant, low intensity stretching in order to develop the patient's full range of motion.

Various dynamic splint mechanisms are described in U.S. Pat. Nos. 4,397,308, 4,485,808, 4,508,111, 1,538,600 and 4,657,000 to George R. Hepburn, all of which are incorporated by these references. The basic design is an adjustable splint assembly comprising a lower strut and an upper strut pivotally connected to said lower strut, one of said struts having at one end a pivotally mounted head portion defining a cam surface, an adjustable biasing means mounted within the other strut and biased into engagement with said cam surface, for applying a quantifiable force tending to align or approximate said upper and lower struts and means for securing said splint assembly to a limb.

Another similar device, Malewicz et. al. U.S. Pat. No. 5,437,619, which is incorporated by this reference, utilizes coil springs as the connection between two sections of a brace to provide a resistance force to motion. However, it can be difficult for the patient to access or adjust the spring tension device while the device is being worn, especially for arm braces.

In another known device, Bonutti U.S. Pat. No. 5,167,612, which is incorporated by this reference, two cuffs are provided for attachment to a patient's limb with a tensioning tower attached between the two cuffs to provide a mechanical advantage for increasing range of motion of the joint. The tower is a box-like structure which includes a drive mechanism for loading and unloading the cuffs to apply force to the limb. The tower device is fairly large and awkward, however, and may not be suited for long term wear by a patient, such as when a patient is sleeping.

Other conventional devices include a rigid element (including a turn buckle) on the inside angle of a joint between two cuffs attached on either side of a joint of a patient's limb and use the turn buckle to vary the length to push or pull the limb segments relative to each other. With this rigid system, the joint is essentially locked at a predetermined position. There is no give or elasticity and as a result, the joint and its tissues fill with lactic acid and cellular waste which pools and leads to discomfort.

Another known device utilizes an airbladder from a blood-pressure cuff to push down one side of a joint while a large cumbersome metal frame and pivotable rod holds the other side of the joint in a fixed relative position. Obvious faults with this device are its extreme bulk and cost of manufacture. Other drawbacks include the inability to stretch a joint in both directions as well as the limited scope of affecting only one joint in the body, the great toe. Yet another drawback of this device is the fact that all joints of the foot are affected during treatment, so that if other digits have been operated on (as is often the case) they will be affected whether or not this is warranted or desired.

Although many of these known adjustable splints operate similarly to each other in applying tension across a joint, they are relatively heavy and bulky and consequently impede, to some extent, free activity at the affected joint. The heavy, tubular strut assemblies used in conventional splints are generally not coextensive from the connecting pivot point, and thus may only be brought into a parallel aligned relationship rather than axially aligned. It is impossible to contour these heavy struts to conform to the limb of a user, and the degree of pivotal movement permitted by such splints is generally much less than 180 degrees. Moreover, misapplied force from a poorly designed or poorly fitting splint can force the limb or digit outside the natural range of motion and destabilize the joint or cause permanent damage to the soft tissues. The distortion of padding and strap attachments, when placed under tension, can result in twisting of the splint's attachments at their intersections with the rigid structural components. This twisting distortion allows the structural components to shift from their desired alignment position, resulting in unintended joint stresses, and uneven distribution of pressure and constriction of soft tissue.

Finally, with known adjustable splints, the bias force adjustment mechanism is often difficult to reach, and the degree of adjustment is often difficult to see. The user must use reading glasses and squint to see the differing levels of force applied. Accurate adjustment of the bias for such splints when they are in place is not easily accomplished either, often requiring fine motor skills to operate small screwdrivers to engage smaller screws that are located inside the device and out of sight. Many patients must have someone do this for them due to the amount of effort required to fit and adjust these splints. Because such splints are generally required to be worn several times per day, it becomes obvious that this is a great difficulty even if the wearer has the luxury of having someone present to assist. Another drawback that stems from the difficulty of putting on and taking off these splints from a lower limb or digit arises when a patient needs to ambulate. This would come in to play if the patient required using the restroom, answering the phone, or getting a drink from the kitchen. In most conventional splints this process would be time consuming and difficult to the point that the patient would consider it too much of a burden to utilize the device.

It would be desirable to provide a device which can be worn by a patient for a long period of time, such as overnight while the patient sleeps, which provides an adjustable, controlled amount of force to the limb to allow for a gradual stretching action. It would also be desirable to use a force adjusting mechanism that has the ability to quickly release undesired or painful force with an easy pull of a tab. Additionally, it would be advantageous to provide a device in which the location of the force applying mechanism can be adjusted to a position where it is easily accessible for adjustment by the patient or in a position where it will cause the least patient discomfort. Yet another advantage would be to have the ability to go from using the device on a right-sided limb or digit to a left with little or no difficulty. Also desirable would be to have a dynamic splint that is lightweight and user friendly, one that can be easily taken to work in a handbag or briefcase and put on and taken off with great ease. And finally, a great advantage of a splint in this field would be to have the versatility to be used for both flexion and extension of a limb or digit as well as to have the adaptability to affect single or multiple digits if required without having to be extensively reconfigured.

III. SUMMARY

The new orthosis separates itself from the above conventional dynamic splints in several ways. For example, a feature of the new orthosis is its superior fit and function. The lighter plastic shell decreases overall unit weight and at the same time allows for some conformability to a limb as opposed to other completely rigid devices. Moreover the lightweight nature of the new orthosis lends itself to be worn with less patient awareness of the device being worn. Another benefit of being lightweight and less bulky is that the new orthosis may be taken to work or on trips with great ease and may even be carried in handbags or briefcases. The lightweight padding accompanying the plastic shell provides great patient comfort as well as preventing skin breakdown and lesions. Furthermore, the padding assists in conforming to an appendage, adding to comfort and performance. Yet another feature of the new orthosis is the convenience and ease of use of the new orthosis, which may be quickly put on or removed in easy steps by oneself—no tensioning tools are needed and there are no tiny screws to fall out. Yet another benefit of the new orthosis is that a patient can easily apply tension and release tension quickly if needed using one hand. Due to the design of the tensioning mechanism, tension can be applied by pulling a lever with one finger; conversely, tension can be released by pulling another lever with a single finger. This not only makes the device easier for a patient to adjust, it makes the unit safer in that improper force can be dissipated almost instantaneously by the flip of a lever. Still another feature of the new orthosis is its durability. Made from plastics, the device can resist damage from impact and has less corrodible parts to be damaged. A key feature of the new orthosis is its versatility in that it can operate in both flexion and extension. Another unique feature is that it can be easily configured to affect single or multiple digits or a user's wrist or ankle by simply adding or removing specially designed end-pieces. Still another unique design benefit is that it can be used ambidextrously (on either right or left appendage) by easily loosening and sliding the tensioning mechanism from the right side of the new orthosis to the left within a channel. Other devices only move in one direction (i.e., flexion) or must be taken apart by a skilled technician and then reassembled and reconfigured in a lengthy time consuming process in order to accommodate the opposite motion (i.e., extension). Still another feature of the new orthosis is the unique tensioning system whereby loosening the tensioning unit and rotating it in relation to the longitudinal axis of the new orthosis, varying angles of force application can be achieved in abduction or adduction.

The new orthosis offers significant advantages and improvements over conventional devices. For example, an advantage of the new orthosis is its cost effectiveness when compared to other devices that utilize more and heavier components. By utilizing better design and production, as well as equally durable yet less expensive plastics, a savings can be passed on to the consumer that cannot be achieved with conventional devices which cost thousands of dollars. Another cost saving benefit stems from the new orthosis's versatility and capability of being easily used on both hands or both feet. Typical conventional devices may only be used on one side of the midsagittal plane.

Yet another benefit of the new orthosis is its being more biophysically correct in that it pulls instead of pushes. This action mirrors the body's natural relationship between muscle tendon and bone in that no movement in the body stems from being pushed. All motion stems from bones being pulled.

Still other features and advantages of the new orthosis will become apparent to those skilled in the art from the following detailed description, wherein one embodiment of the invention is shown and described. It will be apparent to those skilled in the art that various modifications and variations can be made in a joint extension and flexion device according to the invention and in the construction of this device without departing from the scope or spirit of the invention. Other embodiments of the invention will be apparent to those skilled in the art from their consideration of the description of the invention disclosed in this document.

IV. BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 5A-5D illustrate other aspects of the tensioning system of the device shown in FIG. 1.

FIGS. 7A-7C illustrate various aspects of a structure for engaging a single human digit.

FIG. 7D is an exploded partial elevation of one end of the structure illustrated in FIG. 7A and a portion of the connector shown in FIG. 5B.

FIG. 14 illustrates an exemplary new orthosis worn on a user's ankle in a configuration that applies a dorsi-flexion load.

FIG. 15 illustrates an exemplary new orthosis worn on a user's ankle in a configuration that applies a plantar flexion load.

V. DETAILED DESCRIPTION OF THE DRAWINGS

For descriptive clarity and continuity, illustrations depict the new orthosis as applied to a human foot and toes. Functionality and attributes of the new orthosis illustrated are not limited to feet and toes or to human anatomy and apply equally in function and use to other limbs, extremities and digits of the human body.

Another use of the new orthosis described is the prevention or reduction of soft tissue contraction, limiting limb or digit flexion or extension range of motion. Yet another use of the new orthosis is for ambulatory support and rehabilitation. A still further use of the new orthosis is in surgical limb positioning, or for post-operative limb or digit positioning. Another use of the new orthosis is in correcting foot drop due to soft tissue contraction, commonly known as heel-cord shortening. Yet another use of the new orthosis is in soft tissue augmentation for weight bearing therapies.

Figure 1:
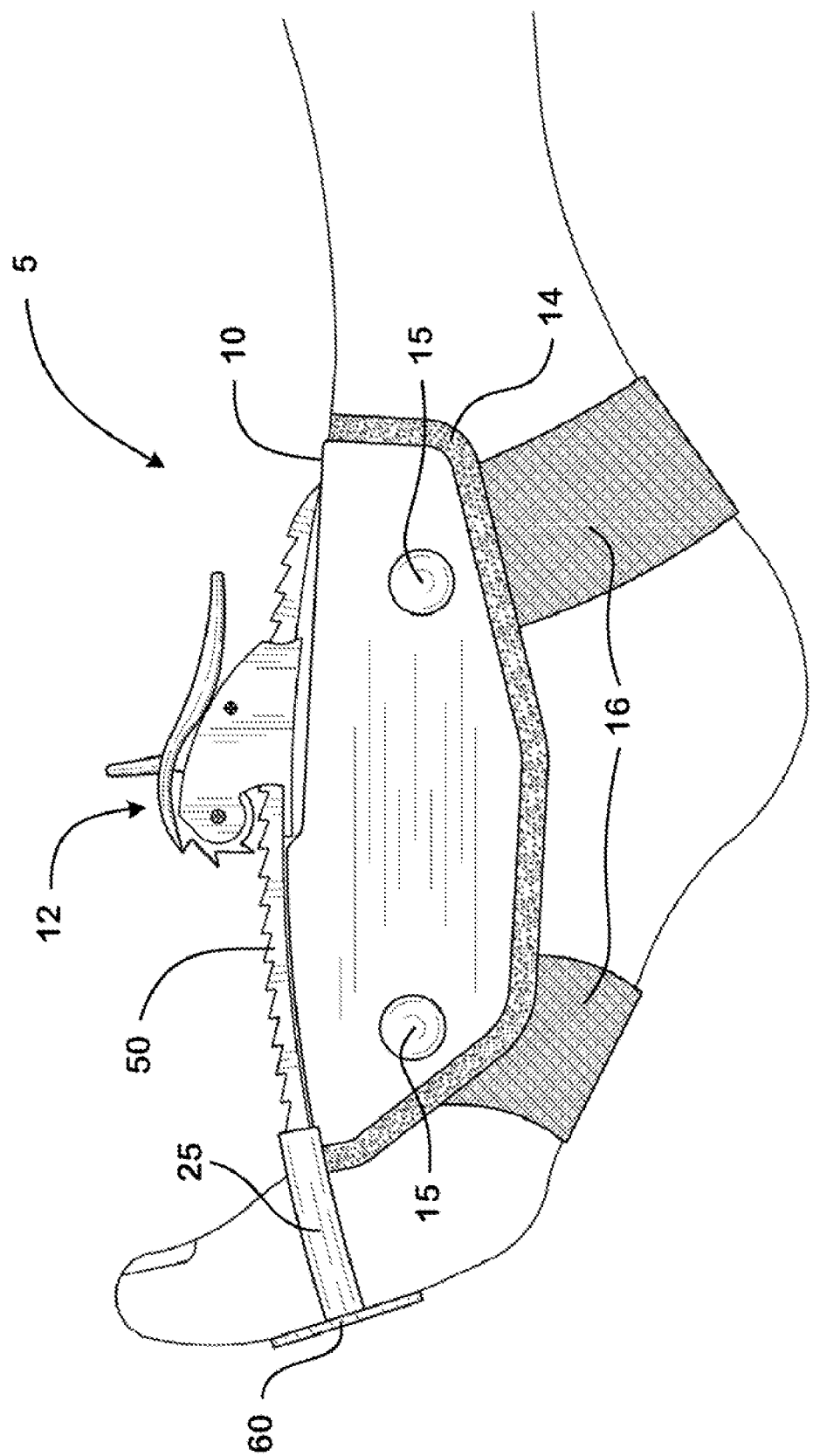
FIG. 1 illustrates an exemplary new orthosis being worn on the foot in a configuration that applies a load to the wearer's big toe to hold the toe in a dorsi-flexion position.
Figure 2A:
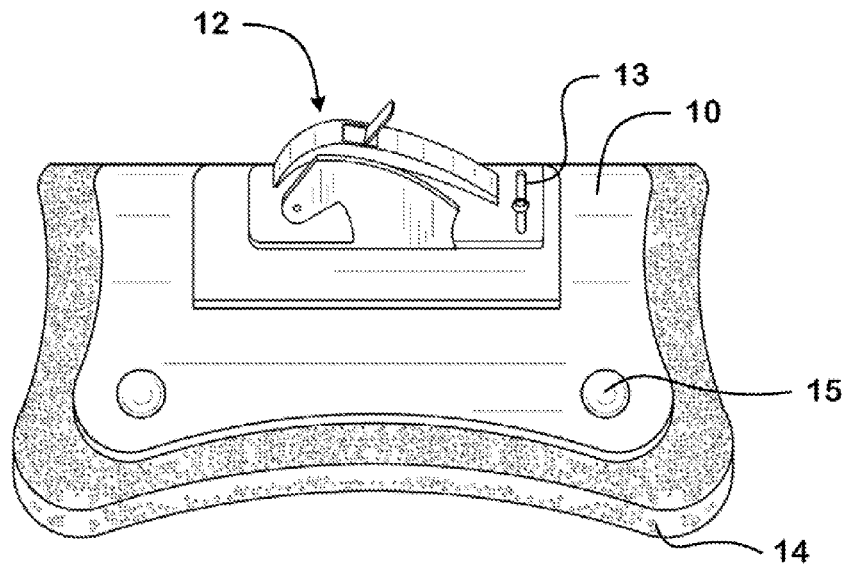
FIGS. 2A-2C illustrate the aspects of the main body and other components of the device of FIG. 1.
Figure 2C:
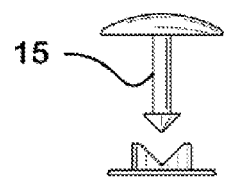
Figure 2B:
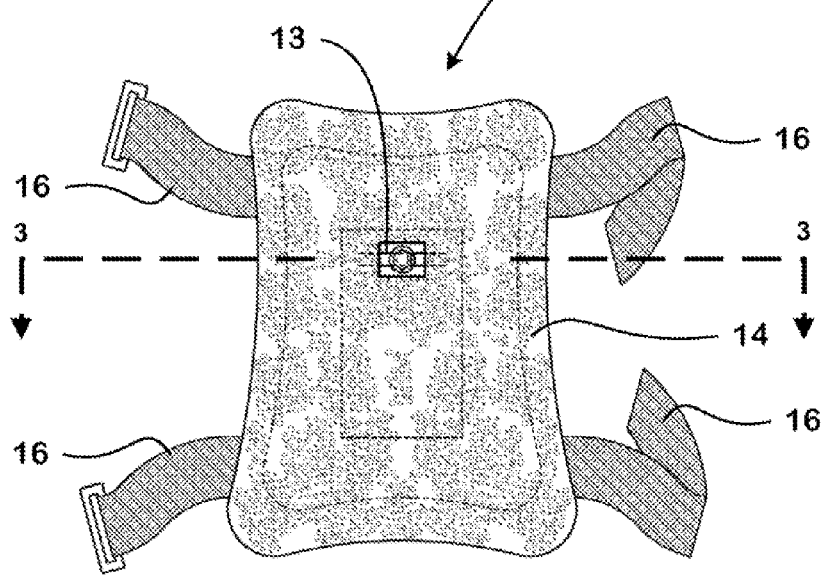

FIG. 1 illustrates one version of a new orthosis 5 being worn on a user's right foot to support the user's big toe in a dorsi-flexion position. The new orthosis 5 shown in FIG. 1 includes a shell 10, tensioning unit 12, padding 14, and straps 16, among other components described below. The main body structure is a rigid yet lightweight plastic that can be injection molded, thermal formed or machine tooled to specifications from polypropylene, ABS plastic or other like material. As shown in FIG. 2, the main body includes a shell 10 that approximates a cylinder cut along a plane that roughly includes the longitudinal axis of the cylinder. The radius of curvature for the shell 10 is smaller on the proximal end that it is on the distal end so that the shell more closely follows the shape of a wearer's body. Additionally, the distal and proximal ends of shell 10 are beveled so that no edges will press into the wearer's skin. This allows the structure to more aptly fit over human appendages which themselves are cylindrical in nature yet of varying circumference at different points. The shell 10 allows for some conformability yet still retains enough rigidity to allow proper support of the tensioning unit 12.

Figure 3:
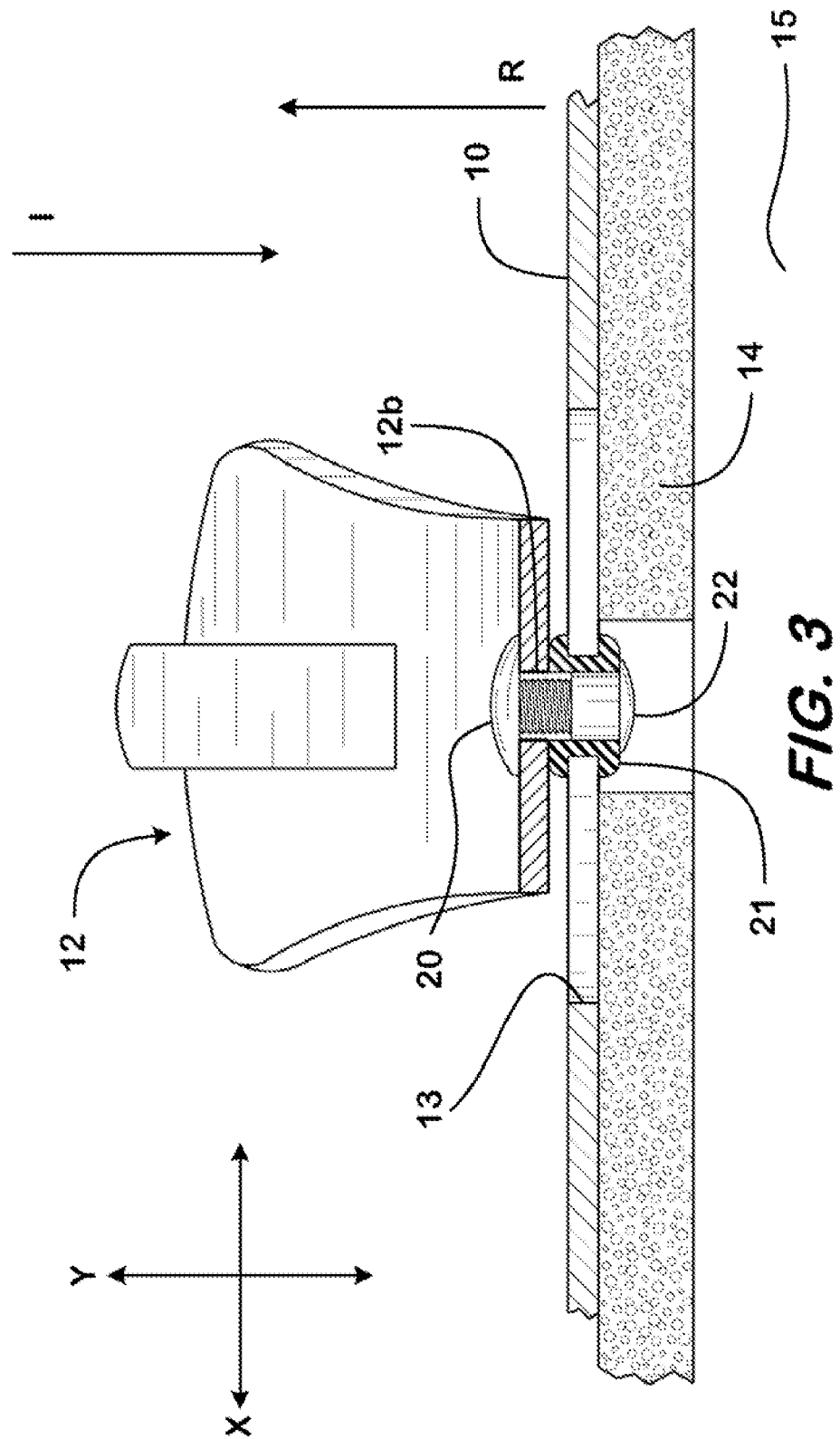
FIG. 3 is a partial cross sectional elevation taken along line 3-3 in FIG. 2B that illustrates aspects of the tensioning system of the device shown in FIG. 1.

FIG. 2 illustrates in more detail portions of the exemplary new orthosis 5 shown in FIG. 1. The tensioning unit 12 includes some type of clasp or other adjustable tensioning mechanism that engages a strap (not shown in FIG. 2). The tensioning unit 12 is connected to the shell 10 as shown in FIG. 3 where a screw head 20 passes through a hole 12b in the tensioning unit 12 into a channel 13 cut into the shell 10 from a superior direction I (shown in FIG. 3). From this point, the screw 20 engages a locking nut 22 which meets the screw from underneath the plastic shell 10 in direction R (shown in FIG. 3). When the screw 20 and locking nut 22 are tightened, the two elements form a connection between the tensioning unit 12 and plastic shell of the body 10. This connection forms a post upon which the tensioning unit 12 may swivel about the Y axis, when not fully tightened. Moreover, when not fully tightened, the post formed by combining screw 20 and locking nut 22 along with the attached tensioning unit 12 may slide from left to right along the X axis. A grommet or bushing 21 may be optionally placed around the post to position the post within channel 13. Upon further tightening of screw 20 into locking nut 22, the two pieces move toward each other from directions I and R as shown on FIG. 3. As screw 20 and locking nut 22 move toward each other, they compress grommet/bushing 21 causing the grommet/bushing 21 to engage shell 10, which tends to hold the tensioning unit 12 in a desired angular position. On the inferior surface and distal end of tensioning unit 12, a strip of neoprene or other non-skid material will be adhered such that when the inferior surface of tensioning unit 12 approximates the superior surface of shell 10, as when being locked in position, the distal end of the tensioning unit 12 will not slide.

As seen in FIG. 2, a pad 14 may be attached to the underside of the shell 10 to increase comfort for the wearer. Pad 14 is preferably constructed of closed cell foam, neoprene or other similar product 14. Preferably, pad 14 is made of a bacteriostatic material or impregnated with a bacteriostatic substance. For example, one type of energy absorbing foam suitable for use as pad 14 is sold by Rogers Corporation as PORON MEDICAL® urethane foam. Pad 14 is preferably breathable and conformable and of sufficient thickness to prevent skin breakdown or lesions from forming at points where force is applied.

Pad 14 may be attached to shell 10 using adhesive (e.g., double-sided tape). Alternatively, pad 14 may be attached to shell 10 using plastic snap rivets 15 by inserting the male half of the rivet through: (1) a hole in the shell 10 and (2) a hole in the pad 14, and (3) an oval shaped hole in the end of a strap 16 beneath pad 14. Once positioned this way, the end of the male half of the rivet is pressed into a corresponding female half of the rivet. Tightly squeezing the halves of the rivets 15 together secures the straps 16, pad 14, and shell 10 together. Preferred materials for shell 10 are ABS, LEXAN®, and ULTEM®. The straps 16 may be padded for comfort with neoprene, felt, or another product similarly cushioning and conformable. The straps 16 may be elastic or non-elastic or a combination of the two. To wear the device, one would position the device on the appropriate portion of the body and connect the ends of the straps 16 to each other with buckles, clasps, hook-and-loop fasteners, or any other suitable connector.

The tensioning system 12 consists of a ratchet type device described in more detail below. However, other similar devices may be used such as those described in U.S. Pat. Nos. 6,748,630; 5,416,952; 5,745,959; 3,662,435; 5,779,259; and 4,547,980, all of which are incorporated by these references. The tensioning system 12 is illustrated in more detail in FIGS. 4A-4D. The tensioning system 12 includes a ratcheting buckle 40 and a corresponding ladder strap 50 that slides through the buckle 40. The tensioning system has a main lever arm 42 with downward facing teeth 46 at one end which engage and pull the upward facing teeth 52 of the ladder strap 50. Lifting up on the lever arm 42 thus drives the teeth 46 and therefore ladder strap 50 in direction I (shown in FIG. 4A), which causes strap 50 to slide further into the buckle 40 and ultimately out the back of the buckle 40. A holding pawl 49 is spring biased to rotate in direction B (shown in FIG. 4A) and keep teeth 52 of strap 50 engaged. Therefore, as strap 50 is inserted in direction I (shown in FIG. 4A), the spring biased pawl 49 engages successive strap teeth 52 in such a way as to hold strap 50 in place and prevent movement in direction R (shown in FIG. 4A). Lifting the end of lever arm 42 will cause teeth 46 to engage strap teeth 52 and move the strap 50 further in direction I (shown in FIG. 4A) until the desired tension in strap 50 is achieved.

The tensioning system 12 also includes a quick release mechanism 44. The wearer manually pulls release tab 44 in direction B (shown in FIG. 4A), which disengages holding pawl 49 from strap teeth 52 and permits strap 50 to be withdrawn from buckle 40 in direction R (shown in FIG. 4A). Pulling quick release tab 44 in direction B (shown in FIG. 4A) also releases any tension that may have been imparted into strap 50 by ratcheting strap 50 in direction I (shown in FIG. 4A) such that it is quickly dissipated.

Figure 4A:
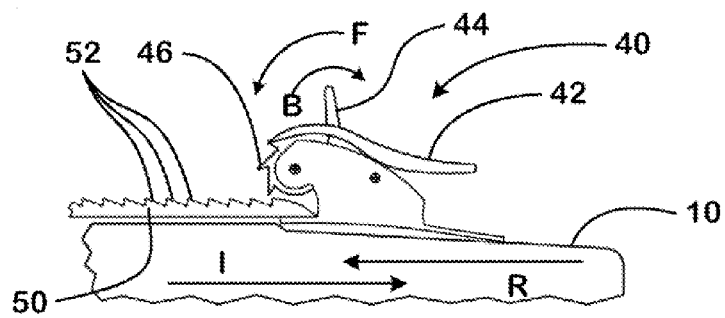
FIGS. 4A-4D illustrate the ratcheting system of the device shown in FIG. 1 and stages of force delivery and release.
Figure 4B:
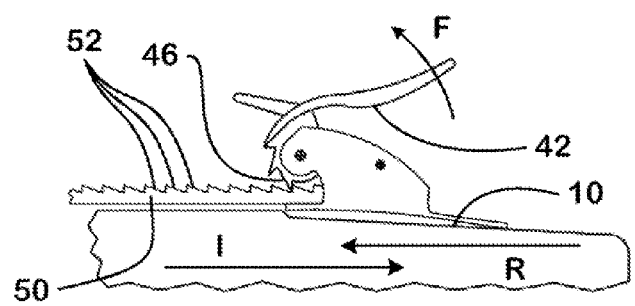
Figure 4C:
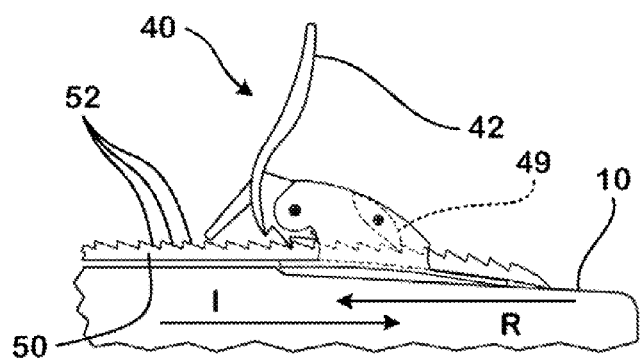
Figure 4D:
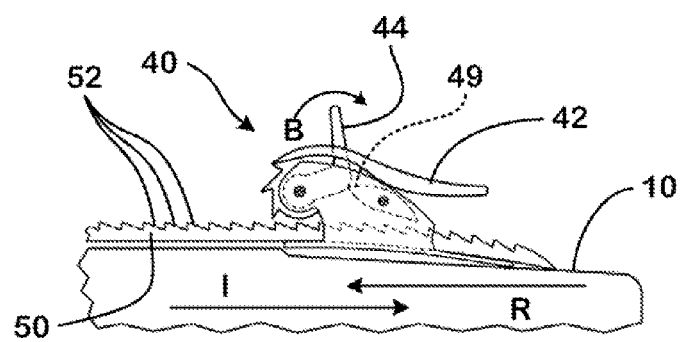
Figure 5D:
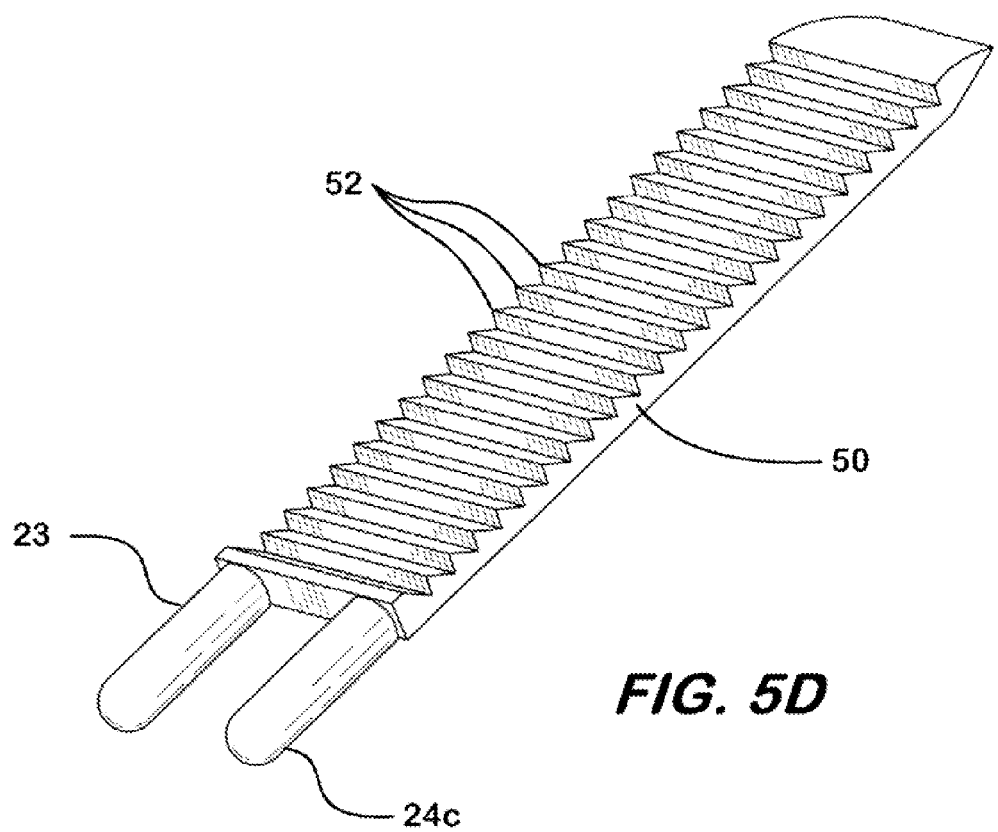

The downward facing teeth 46 of the lever arm 42 are tapered in a saw-tooth shape, and oriented in a circumferential bias to improve the lever arm 42's ability to positively engage the ladder strap's teeth 52 when the lever arm 42 is rotated in direction F (shown in FIGS. 4A-4C). As lever 42 is rotated in direction F, teeth 46 engage teeth 52 and move strap 50 in direction I, which builds tension in tubing 25. To release the tension in tubing 25, lever 44 is moved in direction B (see FIG. 4D) so that it urges pawl 49 to disengage from teeth 52, which lets strap 50 move in direction R. When tubing 25 is stretched as lever 44 is moved in direction B, then the tension in tubing 25 causes strap 50 to move quickly in direction R and release the load imparted by the attached end piece on the wearer's body part. The tensioning unit 12 of the new orthosis can be fabricated from any suitably sturdy materials, including, without limitation, hard polymers, nylon, and metal.

Various embodiments of the strap 50, which is a component of the tensioning system, are illustrated in FIGS. 5A-5D. Strap 50 is made out of a similar material to that of the single digit end piece; hence, it is strong yet flexible. Exemplary types of preferred materials are plastic materials including at least thermoplastics and thermoplastic elastomers including products sold under the brand name KRATON® by GLS Corporation (for greater flexibility) and ABS, LEXAN® and ULTEM® by GE Plastics (for greater stiffness and strength). As mentioned above, strap 50 has upward facing angled teeth 52 that engage the downward angled teeth 46 of the lever arm 42. At one end of the strap 50 are two projections 23 on the proximal end of strap 50. The projections 23 serve as attachment points for surgical tubing 25. The projections 23 may include barbs such as those shown as 24a and 24b or have a smooth surface as is shown by 24c in FIG. 5D. The barbs 24a or 24b engage the tubing and prevent the tubing 25 from being pulled off projections 23 when tension is applied via the ratcheting mechanism. The surgical tubing 25 in the embodiments shown in FIGS. 5A-5D fits over the cylindrical projections 23, and it is preferred to affix tubing 25 to projections 23 with adhesive regardless of the inclusion of barbs 24a or 24b on projections 23.

Surgical tubing 25 adds elasticity to the tension applied by tensioning system 12 to the operative part of the wearer's body. Using surgical tubing 25 to connect the relatively inelastic strap 50 to the wearer's operative body part also introduces a degree of variability in the tension applied because surgical tubing 25 can be characterized as a spring that applies force proportional to the length of stretch from an un-stretched condition. One preferred material for tubing 25 is natural rubber latex. One example of such material is commercially available from Kent Elastomer and is sold as K-911. For relatively small applied strains, surgical tubing 25 behaves approximately like an ideal spring according to Hooke's Law, which states:

$F = -k\Delta x$ in which: F=the force applied to stretch or compress the elastic body k=a "spring constant" associated with the elastic body $\Delta x$=the length that the elastic body has been stretched or compressed from its unloaded condition Therefore, when the wearer tightens the tensioning strap 50, the force applied to the body part will be dynamic depending upon the amount that the tubing 25 has been stretched. The wearer thus can apply force in gradually increasing amounts and with a much greater degree of control over the amount of force being applied. Adding elasticity to the applied tension also results in a more physiologically correct stretch. That is, strap 50, tubing 25, and the various end pieces 30, 60, 70, 80, and 90 apply a tension load to a joint just as muscles apply tension to bone through tendons. Elastic cord, or another elastic material may be used as an alternative to tubing 25.

Figure 6:
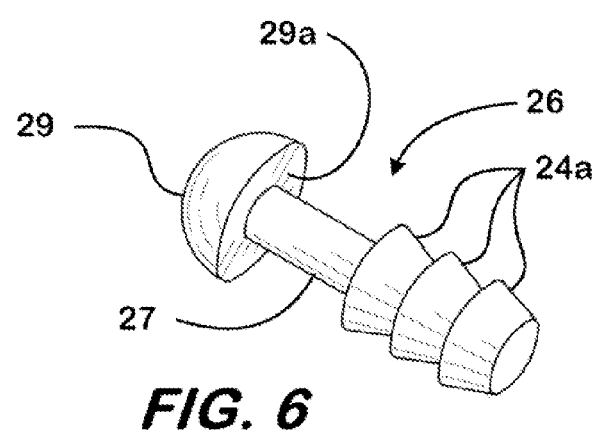
FIG. 6 illustrates in more detail a connector shown in FIG. 5B.

Connector 26 shown in FIG. 5B is illustrated in more detail in FIG. 6. Connector 26, which has reversed barbs 24a at one end and a generally hemispherical head 29 at the other. Connector 26 serves as a bridge between the tubing 25 and the various end-piece attachments illustrated in FIGS. 7A-7C that ultimately engage the operative body part of the wearer. Connector 26 fits within the tubing 25 such that only the male ends 29 protrude outward (see FIG. 5B). Each strap 50 thus includes two sections of surgical tubing 25, with each section having its own connector 26. The protruding male ends have hemispherical heads 29 at their ends which attach (two per device) to the various end pieces that engage the operative body part of the wearer.

The extension and flexion device described above offers an important advantage because both types of end pieces 30 and 34 may be interchangeably attached to the tensioning unit 12 via the fully integrated strap 50 (see FIGS. 5A-5D) thus forming a tensioning system. Devices according to the invention also enable the wearer to stretch a joint in both flexion and extension with relative ease. The wearer can adjust the tension applied to the operative body part using one hand while wearing the device. This, combined with the lightweight nature of the new orthosis, makes it more user-friendly.

Figure 8A:
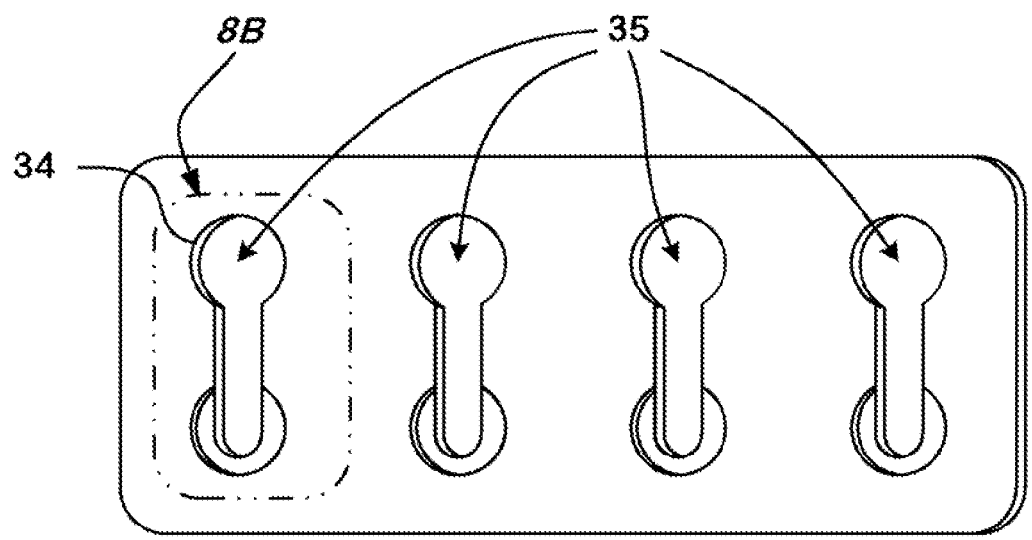
FIGS. 8A and 8B illustrate a structure for engaging two or more human digits with FIG. 8B being a partial exploded view of one of the apertures in the structure shown in FIG. 5A.
Figure 8B:
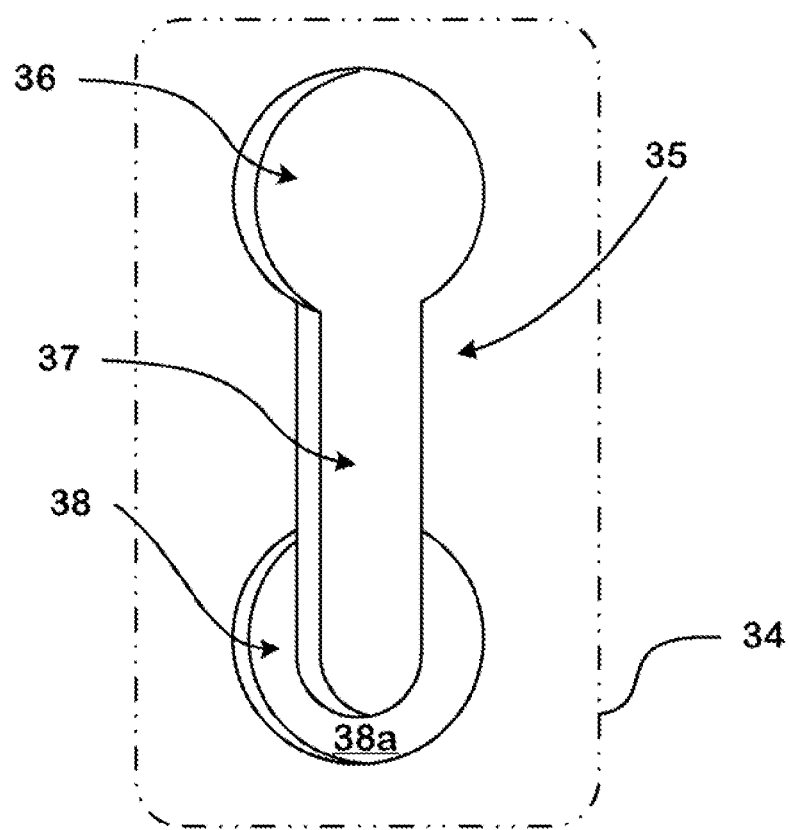

Examples of end pieces that engage the operative body part of the wearer are illustrated in FIGS. 7A-7D, 8A, 8B, and 9-12. The shell 10 and end pieces 70, 80, and 90 illustrated in these figures are constructed of plastics of relatively high strength and stiffness. For example, shell 10 and end pieces 70, 80, and 90 are preferably constructed of ULTEM®, LEXAN® HPS Resin, ABS. End pieces 30 and 60 are constructed of relatively flexible plastics so that they may wrap around a wearer's digit. For example, KRATON® is well suited as a material for end pieces 30 and 60. The end pieces shown in FIGS. 7A-7D and 8A-8B are used in conjunction with the connector 26. End piece 30 is designed to engage a single digit while another version 34 FIG. 8B is designed to engage multiple digits simultaneously. The single-digit end piece 30 is designed to be flexible in order to fit around a single digit. It is preferably composed of plastic that is strong enough to transmit force on a digit yet flexible enough to bend and conform around and between digits. End piece 30 is also preferably lined with padding 33 made of material similar to padding 14. At either end of end piece 30 are female sections 31 which receive the male end 29 of the connector 26 and effectively attach end piece 30 to the tensioning unit 12 via the strap 50. End piece 30 has a female connector block 31 with a channel 32 and an opening adapted to mate with bulbed end 29 of connector 26 as shown in FIG. 7D. With bulbed end 29 positioned above female connector 31, the shaft 27 of the connector 26 slides into the channel 32 of female connector 31 and connector 26 is pulled in direction I so that bulbed end 29 is pulled into female connector 32 until surface 29a contacts surface 31a as shown on FIG. 7D. The force applied by tubing 25 when the new orthosis 5 is in use keeps surface 29a and surface 31a in close proximity. The male end piece 29 of the connector 26 can be removed by pushing connector 26 in direction R until bulbed end 29 clears the female connector 32 so that shaft 27 can be extracted through channel 32.

An exemplary form of a multi-digit end piece is illustrated in FIGS. 8A and 8B. End piece 34 is rectangular with beveled edges and is noticeably more rigid than the single digit end piece 30. Multi-digit end piece 34 is preferably made from thermoplastic or another suitable plastic which can be altered slightly in shape and can be cut to fit individual variances in patient shape or size. In a preferred embodiment, apertures 35 are molded into the end piece 34 at linear intervals from one another. Apertures 35 will ultimately serve as sockets to receive the bulbed end 29 of the connector piece 26. Apertures 35 include a relatively large opening 36, which is slightly larger diameter than the diameter of bulbed end 29 so that the bulbed end 29 may be inserted through opening 36. Apertures 35 also include a channel 37 with approximately the same diameter as the shaft 27 of the connector 26. After bulbed end 29 is inserted through opening 36, the shaft 27 of connector 26 is slid through channel 37 to the bottom of the channel. Once shaft 27 is positioned at the bottom of channel 37, the bulbed end 29 is nestled into the concavity 38 such that surface 29a rests upon surface 38a. This design permits versatility allowing the end user to choose in which channels to put the connector ends. This was designed to accommodate the differing characteristics of peoples' anatomy where the space between one person's second and fourth digit may be completely different from another's. This versatility also enables the treating physician to choose where best to position the end piece 34 in order to deliver the force desired. Due to the unique ball and socket design and the channels of the end piece 34, an advantage of this embodiment is the ability for the end piece 34 to rotate. This allows for greater patient comfort as well as better force distribution as tension is applied to a digit and the end piece 34 moves along with the digit in proper joint motion.

The embodiments of end pieces 60, 70, 80, and 90 shown in FIGS. 9-12 are not used in conjunction with connector 26. Instead, end pieces 60, 70, 80, and 90 connect directly to tubing 25 via projections 62, 72, 82, and 92 respectively.

Figure 9:
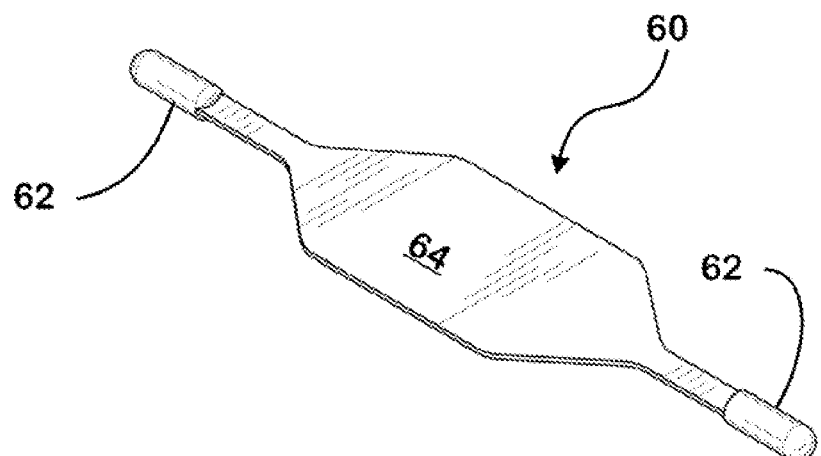
FIG. 9 illustrates an embodiment of an end piece, which is best suited for use with a single digit on a wearer's hand or foot.

FIG. 9 illustrates end piece 60, which is best suited for use with a single digit on a wearer's hand or foot. End piece 60 includes support surface 64, which would contact a user's body when device worn by the user and transfer loads imparted by end piece 60 to the targeted body part. End piece 60 connects directly to tubing 25 via projections 62, which are integrally molded structures with the remainder of end piece 60. Otherwise, end piece 60 is similar to end piece 30 illustrated in FIGS. 7A-7D.

Figure 10:
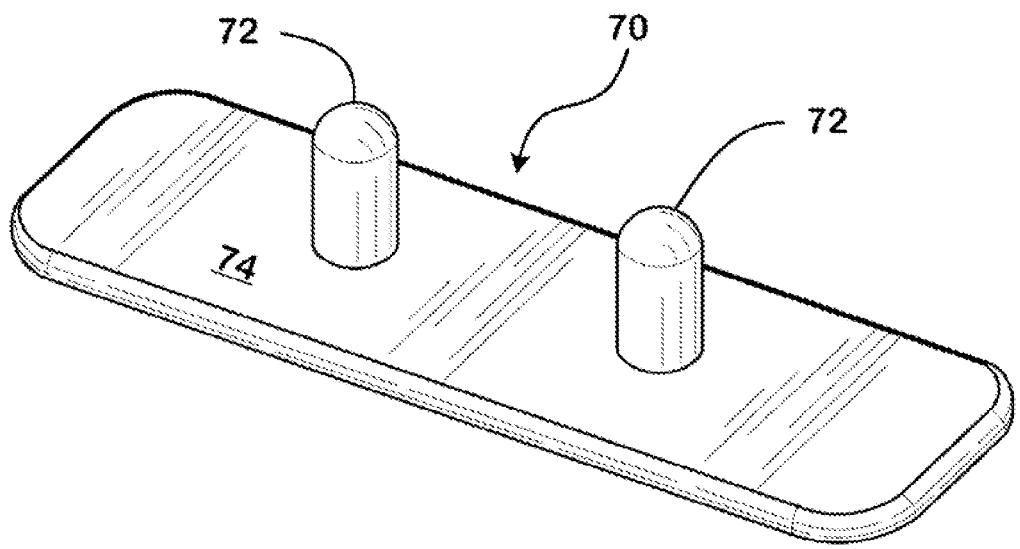
FIG. 10 illustrates an embodiment of an end piece, which is best suited for use with multiple digits on a wearers hand or foot.

FIG. 10 illustrates end piece 70, which is best suited for use with multiple digits on a wearer's hand or foot. End piece 70 includes support surface 74, which would contact a user's body when device worn by the user and transfer loads imparted by end piece 70 to the targeted body part. End piece 70 connects directly to tubing 25 via projections 72, which are integrally molded structures with the remainder of end piece 70. Otherwise, end piece 70 is similar to end piece 34 illustrated in FIGS. 8A-8B. End piece 70 is preferably molded of a relatively stiff plastic such as ULTEM®, LEXAN® HPS Resin, or ABS.

Figure 11:
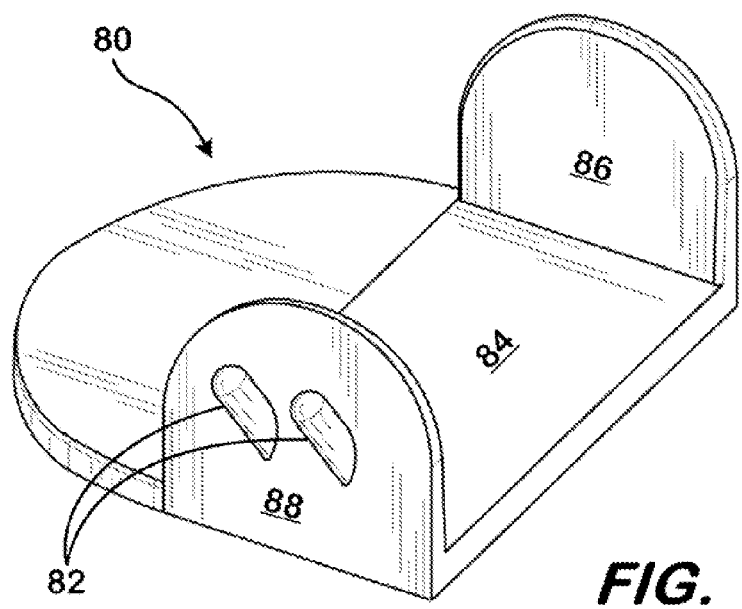
FIG. 11 illustrates an embodiment of an end piece, which is best suited as a support for a wearer's entire hand or entire foot.

FIG. 11 illustrates end piece 80, which is adapted to support a wearer's entire foot while flexing or extending a wearers ankle joint as needed. End piece 80 is worn as part of a new orthosis 5 as shown, for example, in FIGS. 14 and 15. End piece 80 includes support surfaces 84 and 86, which would contact a user's foot when the device is worn by the user. Surface 84 provides primary support for the wearer's foot and transfers loads imparted by end piece 80 to the foot. When tubing 25 is pulled by tensioning unit 40, part of the tension in tubing 25 is translated into forces against the side of the wearer's foot. Surface 86 cushions the sides of the wearer's foot from such side loads and distributes these side loads more evenly over the entire surface area of surfaces 86. Surfaces 84 and 86 optionally may be lined with padding (not shown) made using the same materials described above in connection with pad 14. End piece 80 connects directly to tubing 25 via projections 82, which are integrally molded structures with the remainder of end piece 80. End piece 80 preferably includes four projections 82, with a pair of projections 82 protruding from each of surfaces 88. With four projections 82 and therefore four pieces of tubing 25. Tubing 25 is also attached to a strap 50, which adjustably mates with the tensioning unit 40. Because four pieces of tubing 25 are used, the new orthosis 5 is able to impart higher extension or flexion loads on the wearer's foot. Such higher loads (when compared to the loads required to position the digits on a hand or foot) are required to position the wearer's foot in the desired therapeutic position. End piece 80 is made of the same type of materials described above in connection with end piece 70. However, end piece 80 is preferably stiffer than end piece 70.

Figure 12:
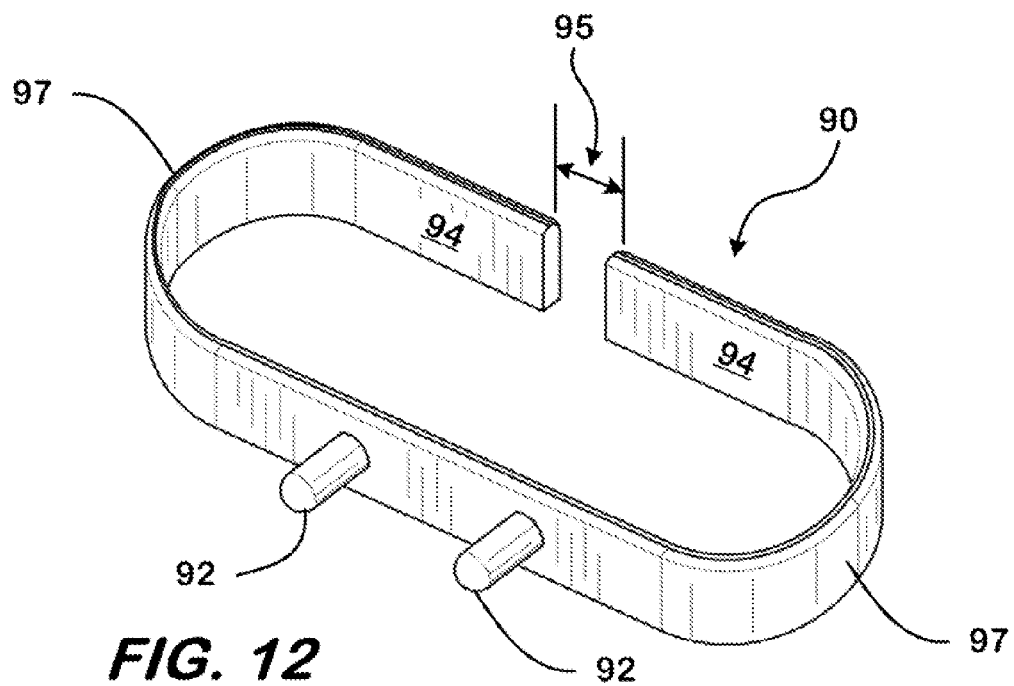
FIG. 12 illustrates an embodiment of an end piece, which is best suited as a support for a wearer's entire hand.

FIG. 12 illustrates a ring-shaped end piece 90, which is adapted to support a wearer's entire hand while flexing or extending a wearer's wrist joint as needed. End piece 80 is worn as part of a new orthosis 5 as shown, for example, in FIG. 13. End piece 90 includes support surfaces 94, which would contact a user's hand when device worn by the user. Surface 94 provides primary support for the wearer's hand and transfers loads imparted by end piece 90 to the hand. Surfaces 94 optionally may be lined with padding (not shown) made using the same materials described above in connection with pad 14. End piece 90 connects directly to tubing 25 via projections 92, which are integrally molded structures with the remainder of end piece 90. Tubing 25 is also attached to a strap 50, which adjustably mates with the tensioning unit 12. End piece 90 includes a gap 95 between surfaces 94, which adds further resiliency to the end piece and permits end piece 90 to accommodate hands of larger size by permitting sides 97 of end piece 90 to spread apart. Once a wearer's hand is positioned inside end piece 90, the gap 95 is stabilized with an adjustable strap (not shown) that connects via complementary hook and loop connectors on opposing sides of gap 95. End piece 90 is made of the same type of materials described above in connection with end piece 70.

Figure 13:
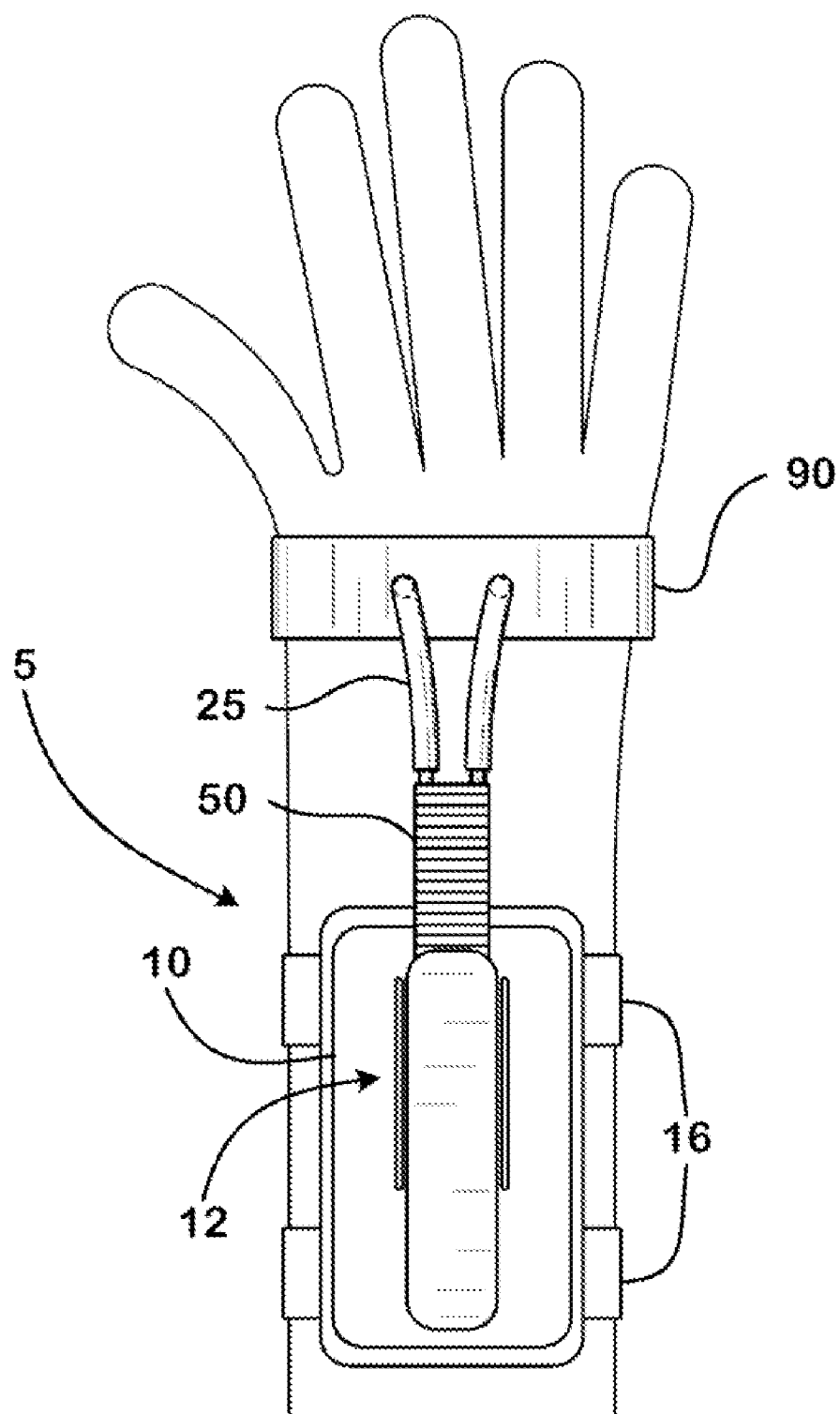
FIG. 13 illustrates an exemplary new orthosis worn on a user's wrist with using the end piece of FIG. 12 to apply an exemplary flexion load.

FIGS. 13-15 illustrate various ways in which a user might wear the new orthosis 5. FIG. 13 illustrates the new orthosis 5 worn on a user's wrist with shell 10 positioned on the dorsal aspect of the user's forearm and end piece 90 positioned on the dorsal aspect of the hand so that tensioning unit 12 can apply load to the hand and extend the wearer's wrist.

FIG. 14 illustrates the new orthosis 5 worn on a user's lower leg. Tensioning unit 12 is positioned on the shin such that strap 50 extends toward the top of the wearer's forefoot as shown. The tensioning unit 12 applies a load to the forefoot via tubing 25 connected to end piece 80 to dorsi-flex the ankle.

FIG. 15 illustrates the new orthosis 5 worn on a user's lower leg. Tensioning unit 12 is positioned on the back of the lower leg such that strap 50 extends around the wearer's heel. The tensioning unit 12 applies a load to the forefoot via tubing 25 connected to end piece 80 to plantar flex the ankle.

Alternatively, new orthosis 5 shown in FIGS. 14 and 15 could have two tensioning units 12, one positioned on the medial aspect of the lower leg and another positioned on the lateral aspect of the lower leg. The medial tensioning unit would be connected via tubing 25 to projections 82 on the medial side of end piece 80. The lateral tensioning unit would be connected via tubing 25 to projections 82 on the lateral side of end piece 80. In such an arrangement the amount of tension applied to the medial and lateral aspects of the wearer's foot could be controlled separately.

Although the invention has been described with reference to specific embodiments, this description is not meant to be construed in a limiting sense. Various modifications of the disclosed embodiment, as well as alternative embodiments of the invention, will become apparent to one skilled in the art upon reference to the description of the invention. It is therefore contemplated that the appended claims will cover any such modifications of embodiments that fall within the true scope of the invention.

What is claimed is:

1. An orthosis for selectively flexing or extending a joint of a user, comprising:
   A. a first support that is adapted to be worn by the user on a first body part located on a first side of the joint;
   B. an adjustable fastener connected to the first support;
   C. a connector, comprising:
      i. a flexible strap having:
         a. a first strap end portion adapted to mate with the adjustable fastener and
         b. a second strap end portion, and
      ii. an elastic member, comprising a first elastic tube and a second elastic tube and having:
         a. a first elastic end portion connected to the strap near the second strap end portion and
         b. a second elastic end portion generally opposite the first elastic end portion;
   D. a second support adapted to be worn by the user on a second body part located on the opposite side of the joint to the first side of the joint having a first projection that is connected to the first elastic tube near the second strap end portion and a second projection that is connected to the second elastic tube near the second strap end portion.

2. The orthosis of claim 1, in which the second support comprises a ring-shaped member adapted to support the user's hand.

3. The orthosis of claim 2, in which the ring-shaped member includes a gap to permit the ring-shaped member to accommodate hands of varying sizes.

4. The orthosis of claim 1, in which:
   A. the flexible strap further comprises a plurality of strap teeth located on a surface of the first strap end portion; and
   B. the adjustable fastener is a ratcheting device comprising:
      i. a ratchet body;
      ii. a lever arm connected to the ratchet body with at least one pulling tooth on one end that selectively engages the plurality of strap teeth, and
      iii. at least one holding tooth connected to the ratchet body that engages at least one of the plurality of strap teeth.

5. The orthosis of claim 4 in which the ratcheting device further comprises a quick release lever connected to the ratchet body that selectively engages the holding tooth to cause the holding tooth to disengage from the at least one of the plurality of strap teeth.

6. The orthosis of claim 1, in which the second support comprises a sling adapted to support one of the user's digits on the user's hand or foot.

7. The orthosis of claim 1, in which the second support comprises a digit shell adapted to support at least two of the user's digits on the user's hand or foot.

8. The orthosis of claim 1, in which the second support comprises a forefoot shell adapted to support the user's forefoot.

9. The orthosis of claim 8, in which the forefoot shell further comprises:
   A. a primary support member,
   B. a first side support member connected to the primary support member along a first edge, and
   C. a second side support member connected to the primary support member along a second edge substantially opposite the first edge.

10. The orthosis of claim 1, in which the first support comprises:
   A. a relatively stiff first shell shaped to conform approximately to a portion of the user's first body part;
   B. a pad connected to the first shell and positioned between the first shell and the user's first body part when the orthosis is worn by the user; and C. a first adjustable support strap adapted to wrap around the first body part and secure the first support to the first body part.

11. An orthosis for selectively flexing or extending a joint of a user, comprising:
   A. a first support that is adapted to be worn by the user on a first body part located on a first side of the joint, comprising:
      i. a relatively stiff first shell shaped to conform approximately to a portion of the user's first body part;
      ii. a pad connected to the first shell and positioned between the first shell and the user's first body part when the orthosis is worn by the user; and
      iii. a first adjustable support strap adapted to wrap around the first body part and secure the first support to the first body part;
   B. an adjustable fastener connected to the first support;
   C. a connector, comprising:
      i. a flexible strap having:
         a. a first strap end portion adapted to mate with the adjustable fastener and
         b. a second strap end portion, and
      ii. an elastic member comprising a first elastic tube and a second elastic tube and having:
         a. a first elastic end portion connected to the strap near the second strap end portion and
         b. a second elastic end portion generally opposite the first elastic end portion; and
   D. a second support, comprising:
      i. a ring-shaped member adapted to support the user's hand;
      ii. a first projection that is inserted into the first elastic tube, and
      iii. a second projection that is inserted into the second elastic tube.

12. The orthosis of claim 11, in which the ring-shaped member includes a gap to permit the ring-shaped member to accommodate hands of varying sizes.

13. An orthosis for selectively flexing or extending a joint of a user, comprising:
   A. a first support that is adapted to be worn by the user on a first body part located on a first side of the joint, comprising:
      i. a relatively stiff first shell shaped to conform approximately to a portion of the user's first body part;
      ii. a pad connected to the first shell and positioned between the first shell and the user's first body part when the orthosis is worn by the user; and
      iii. a first adjustable support strap adapted to wrap around the first body part and secure the first support to the first body part;
   B. an adjustable fastener connected to the first support;
   C. a connector, comprising:
      i. a flexible strap having:
         a. a first strap end portion adapted to mate with the adjustable fastener and
         b. a second strap end portion, and
      ii. an elastic member, comprising a first elastic tube and a second elastic tube and having:
         a. a first elastic end portion connected to the strap near the second strap end portion,
         b. a second elastic end portion generally opposite the first elastic end portion,
   D. a second support, comprising:
      i. a first projection that is inserted into the first elastic tube, and
      ii. a second projection that is inserted into the second elastic tube, in which the second support is:
         a. adapted to be worn by the user on a second body part located on the opposite side of the joint to the first side of the joint and support one of the user's digits on the user's hand or foot,
         b. connected to the elastic member near the second elastic end portion, and
         c. not otherwise connected to the first support.

14. An orthosis for selectively flexing or extending a joint of a user, comprising:
   A. a first support that is adapted to be worn by the user on a first body part located on a first side of the joint, comprising:
      i. a relatively stiff first shell shaped to conform approximately to a portion of the user's first body part;
      ii. a pad connected to the first shell and positioned between the first shell and the user's first body part when the orthosis is worn by the user; and
      iii. a first adjustable support strap adapted to wrap around the first body part and secure the first support to the first body part;
   B. an adjustable fastener connected to the first support;
   C. a connector, comprising:
      i. a flexible strap having:
         a. a first strap end portion adapted to mate with the adjustable fastener and
         b. a second strap end portion, and
      ii. an elastic member comprising a first elastic tube and a second elastic tube and having:
         a. a first elastic end portion connected to the strap near the second strap end portion and
         b. a second elastic end portion generally opposite the first elastic end portion;
   D. a second support, comprising:
      i. a digit shell adapted to support at least two of the user's digits on the user's hand or foot;
      ii. a first projection that is inserted into the first elastic tube,
      iii. a second projection that is inserted into the second elastic tube, in which the second support is:
         a. adapted to be worn by the user on a second body part located on the opposite side of the joint to the first side of the joint,
         b. connected to the elastic member near the second elastic end portion, and
         c. not otherwise connected to the first support.

15. An orthosis for selectively flexing or extending a joint of a user, comprising:
   A. a first support that is adapted to be worn by the user on a first body part located on a first side of the joint, comprising:
      i. a relatively stiff first shell shaped to conform approximately to a portion of the user's first body part;
      ii. a pad connected to the first shell and positioned between the first shell and the user's first body part when the orthosis is worn by the user; and
      iii. a first adjustable support strap adapted to wrap around the first body part and secure the first support to the first body part;
   B. an adjustable fastener connected to the first support;
   C. a connector, comprising:
      i. a flexible strap having:
         a. a first strap end portion adapted to mate with the adjustable fastener and
         b. a second strap end portion, and ii. an elastic member comprising a first elastic tube and a second elastic tube and having:
   a. a first elastic end portion connected to the strap near the second strap end portion and
   b. a second elastic end portion generally opposite the first elastic end portion; and
D. a forefoot shell adapted to support the user's forefoot, comprising:
   i. a primary support member,
   ii. a first side support member connected to the primary support member along a first edge,
   iii. a second side support member connected to the primary support member along a second edge that is substantially opposite the first edge,
   iv. a first projection on the first side support member that is connected to the first elastic, and
   v. a second projection on the second side support member that is connected to the second elastic tube.

16. An orthosis for selectively flexing or extending a joint of a user, comprising:
A. a first support that is adapted to be worn by the user on a first body part located on a first side of the joint, comprising:
   i. a relatively stiff first shell shaped to conform approximately to a portion of the user's first body part;
   ii. a pad connected to the first shell and positioned between the first shell and the user's first body part when the orthosis is worn by the user; and
   iii. a first adjustable support strap adapted to wrap around the first body part and secure the first support to the first body part;
B. a connector, comprising:
   i. a flexible strap having:
      a. a first strap end portion having a plurality of strap teeth located on a surface of the first strap end portion;
      b. a second strap end portion, and
   ii. an elastic member, comprising a first elastic tube and a second elastic tube and having:
      a. a first elastic end portion connected to the strap near the second strap end portion,
      b. a second elastic end portion generally opposite the first elastic end portion,
C. a ratcheting device connected to the first support, comprising a;
   i. a ratchet body;
   ii. a lever arm connected to the ratchet body with at least one pulling tooth on one end that selectively engages the plurality of strap teeth,
   iii. at least one holding tooth connected to the ratchet body that engages at least one of the plurality of strap teeth,
   iv. a quick release lever connected to the ratchet body that selectively engages the holding tooth to cause the holding tooth to disengage from the at least one of the plurality of strap teeth,
D. a second support, comprising:
   i. a first projection that is inserted into the first elastic tube, and
   ii. a second projection that is inserted into the second elastic tuber, and in which the second support is:
      a. adapted to be worn by the user on a second body part located on the opposite side of the joint to the first side of the joint,
      b. connected to the elastic member near the second elastic end portion,
      c. not otherwise connected to the first support.

* * * * *